United States Patent [19]

Christensen

[11] Plant 5,177

[45] Jan. 17, 1984

[54] ROSE PLANT CV. AROYQUELI

[75] Inventor: Jack E. Christensen, Ontario, Calif.

[73] Assignee: Armstrong Nurseries, Inc., Ontario, Calif.

[21] Appl. No.: 413,831

[22] Filed: Sep. 1, 1982

[51] Int. Cl.[3] ..... A01H 5/00

[52] U.S. Cl. ..... Plt./15

[58] Field of Search ..... Plt./15

*Primary Examiner*—James R. Feyrer

*Attorney, Agent, or Firm*—Synnestvedt & Lechner

[57] ABSTRACT

A new variety of hybrid grandiflora rose plant, of the hardy outdoor, tall bush type. This new rose cultivar is unique and distinguishable from existing rose cultivars by the following combination of characteristics: its deep yellow gold coloration lasts well throughout the life of the flower; its vigor and profusion of flowers provides an easy-to-grow, satisfying garden plant; its abundant large foliage attractively clothes the entire plant; its above average hardiness and disease resistance are especially unique among other yellow roses; its true grandiflora habit is unusual among yellow roses; its profusion of strong-stemmed flowers lends the variety well to the production of long-stemmed bouquets cut from the garden; its classically spiraled flower form is very consistent in a wide climatic range; its abundant production of basal canes lends to the overall attractive bushy habit; its nearly continual production of flowers throughout the growing season.

1 Drawing Figure

1

This invention relates to a new variety of hybrid grandiflora rose cv. Aroyqueli. The plant is a hardy, tall, bushy outdoor seedling, grown mainly for garden decoration. It was asexually reproduced by Jack E. Christensen in Ontario, Calif., having as its seed parent "Yellow Pages" (unpatented) and for its pollen parent, an undisseminated seedling of "Granada×Garden Party" (also unpatented). The new variety holds its distinguishing characteristics through succeeding propagations by budding.

This new rose cultivar is unique and distinguishable from existing rose cultivars by the following combination of characteristics: its deep yellow gold coloration lasts well throughout the life of the flower; its vigor and profusion of flowers provides an easy-to-grow, satisfying garden plant; its abundant large foliage attractively clothes the entire plant; its above average hardiness and disease resistance are especially unique among other yellow roses; its true grandiflora habit is unusual among yellow roses; its profusion of strong-stemmed flowers lends the variety well to the production of long-stemmed bouquets cut from the garden; its classically spiraled flower form is very consistent in a wide climatic range; its abundant production of basal canes lends to the overall attractive bushy habit; and its nearly continual production of flowers throughout the growing season.

The plant bears its flowers sometimes singly, usually three or more to a stem in regular rounded clusters on strong, long stems. It blooms abundantly outdoors, and nearly continuously during the growing season. The blooms have a moderate spicy fragrance.

Among the ways in which this new cultivar may be most readily distinguished from its seed parent, Yellow Pages, are the following.

Whereas Yellow Pages bears flowers with approximately 50 petals, the new cultivar bears flowers of significantly less petalage (from 33 to 40), essentially as described below and illustrated herein.

Yellow Pages produces a bush with small, very glossy foliage, whereas the new cultivar has significantly larger foliage with a semi-glossy appearance.

2

Whereas Yellow Pages is classified as a hybrid tea (producing flowers singly on most stems), the new rose cv. Aroyqueli is classified as a hybrid grandiflora.

The new rose cultivar produces a tall ($4\frac{1}{2}$ to $5\frac{1}{2}$ feet) well-branched bush, whereas Yellow Pages produces a significantly shorter bush (3 to 4 feet) under Ontario, Calif. growing conditions.

This new cultivar may most readily be distinguished from its pollen parent, an undisseminated seedling of Granada×Garden Party, by the following characteristics.

Whereas the undisseminated seedling parent bears flowers of a light yellow-edged pink coloration, the new cultivar bears flowers of significantly deeper yellow coloration essentially as described and illustrated herein.

The new rose bears flowers of average size (4 to $4\frac{1}{2}$ inches), whereas the seedling parent bears significantly larger flowers (5 to 6 inches).

Whereas the new cultivar is classified as a hybrid grandiflora, the seedling parent is classified as a hybrid tea.

Whereas the undisseminated seedling bears flowers with a strong sweetbriar fragrance, the new rose cultivar bears flowers with significantly less fragrance.

The accompanying drawing illustrates the plant in color and shows the flowering thereof from bud to full bloom.

Throughout this specification color names beginning with a small letter signify that the name of that color, as used in common speech, is aptly descriptive. Color names beginning with a capital letter designate values based upon the R.H.S. Colour Chart published by The Royal Horticultural Society of London, England.

BUD

The peduncle is of short to average length, average caliper, erect and stiff. It is moderately smooth, with some stipitate glands.

Before the calyx breaks, the bud is of medium size, medium to long length, pointed, ovoid, and with some foliaceous appendages on the surface of the bud. Usually there are slender foliaceous parts extending beyond the tip of the bud equal to one-half or more of its length.

As the calyx breaks, the color is near Yellow, 12B.

The inner surface of the sepals carries a fine, wooly tomentum; margins are lined with hairs.

As the first petal opens, the bud is of average size, medium to long length, and pointed ovoid to urn-shaped. The color on the outside of the petal is between Yellow-Orange, 15B and Yellow-Orange, 14C and areas exposed to sunlight blush to between Orange, 24B and Orange, 28C. The color on the inside of the petal is between Yellow-Orange, 14B and Yellow-Orange, 14C. The bud opens up well, and is not prevented from opening by cold, hot, wet or dry weather.

BLOOM

When fully open, the bloom is of average to large size, being from 4 to 4½ inches in diameter. The petalage is double, with from 33 to 40 petals, plus from 1 to 5 petaloids arranged regularly. In form, the bloom is high centered at first, becoming cupped to high centered; the petals are first tightly cupped, becoming later at maturity loosely cupped, with tips reflexed outward.

PETALS

The petals are of medium thickness, with the inside slightly satiny and the outside slightly shiny.

The outside petals are from round to broadly obovate, and have a flat apex. Intermediate petals are broadly obovate, and with the apex rounded. The inside petals are narrowly obovate and have an irregular apex. Color may be modified by being bordered, shaded and/or washed or tinted with other colors.

The following description is of a newly opened rose that had been grown outdoors in the month of July in Ontario, Calif.

The coloration of the outer surface of the outside petal was between Yellow, 13B and Yellow-Orange, 16B, sometimes suffused with between Orange, 24B and Orange, 28C. The inside surface of the outside petal was of a coloration between Yellow-Orange, 14B and Yellow-Orange, 16B; areas exposed to sunlight sometimes blush to near Orange, 28C.

The inside and outside surfaces of the intermediate petals have the same coloration as the corresponding inside and outside surfaces of the outside petals but with less blushing.

The inside and outside surfaces of the inner petals have the same coloration as the corresponding inside and outside surfaces of the outside petals but with no blushing.

The following description was made from a rose that was open for three days outdoors in the month of July. The plant had been grown in Ontario, Calif.

Both the outside and the inside petals were of the same coloration. The outer surface was between Yellow, 12C and Yellow-Orange, 16D. The inner surface was the same coloration but sometimes blushed with between Orange, 29D and Orange 27A.

The general color effect of the newly opened flower was between Yellow-Orange, 14B and Yellow-Orange, 16B sometimes blushed with between Orange, 24B and Orange 28C. After being three days open, the flower was between Yellow, 12C and Yellow-Orange, 16D and is sometimes lightly blushed with between Orange, 29D and Orange, 27A. Petals drop off cleanly. The plant is not particularly affected by cold, hot, wet or dry weather.

The flower on the bush in the garden persists for from 3 to 5 days in the month of July. Cut roses grown outdoors and kept at living-room temperatures last from 4 to 6 days in the month of July.

REPRODUCTIVE ORGANS

There are from an average number to many stamens arranged regularly about the pistils.

The filaments are of medium-length. Most are with anthers.

Anthers are of medium size and all open approximately at once. Their color when immature is near Yellow-Orange, 15A and near Greyed-Orange, 165A when mature.

Pollen is moderate and the color is near Yellow-Orange, 16C.

There are from a few to an average number (approximately 35) of pistils.

Styles are uneven, of short to average length, of average caliper and loosely bunched.

The stigma coloration is near Yellow, 5D.

The ovaries are usually enclosed in the calyx.

The hips are of short to average length, globular, very smooth and have fleshy walls.

The sepals are permanent, long and spear-shaped; the inside coloration is near Green, 138B and the outside coloration is near Green, 138A.

The seeds are large and are few to average (6 to 15) in number.

FOLIAGE

The compound leaves usually comprise from three to five leaflets. They are abundant, of large size, heavy and semi-glossy. The leaflets are ovate in shape, with apex acuminate, base acute and margin simply serrate.

The upper surface of the mature foliage is a color between Green, 137B and Green, 136A. The under surface is between Green, 138B and Yellow-Green, 147C.

The upper surface of young foliage had the same coloration as the upper surface of mature foliage but heavily suffused with near Greyed-Purple, 184A. The under surface showed a coloration between Greyed-Purple, 183D and Greyed-Red, 178B.

The rachis is average in size, grooved on its upper side, with some stipitate glands on the edges. The under side is extremely smooth.

The stipules are medium to long in length and of narrow to medium width, with medium-length points turning out at an angle of less than 45°.

The plant displays a more than average resistance to mildew and blackspot as compared to other varieties grown under Ontario, Calif. growing conditions.

GROWTH

The plant is bushy and upright in habit, and much branched. It displays a very vigorous growth. Canes are of medium to heavy caliper.

The main stems are between Yellow-Green, 146C and Yellow-Green, 147C in color. They bear a few large prickles, which are short to medium-length, almost straight and with a medium-length moderately broad base. Their color is near Greyed-Orange, 165A. There are no small prickles and no hairs.

The branches have a coloration which is between Green, 137D and Yellow-Green, 146B, side exposed to sunlight sometimes blushes to between Greyed-Orange, 177A and Greyed-Orange, 176A. They carry a few large prickles, which are of short to medium-length, almost straight and with a medium length, moderately broad base. Their coloration is between Greyed-Orange, 164A and Greyed-Orange, 165A. There are no small prickles and no hairs.

The new shoots are between Green, 137D and Yellow-Green, 146B in color; they are heavily suffused with between Greyed-Purple, 183D and Greyed-Red, 178B. They bear several large prickles, which are of short to medium length, almost straight, with a medium-length, moderately broad base. Their color is between Greyed-Purple, 183C and Greyed-Red, 178A. There are no small prickles and no hairs.

I claim:

1. A new and distinct variety of rose plant of the hybrid grandiflora class, substantially as herein shown and described, being further especially characterized in that its deep yellow gold coloration lasts well throughout the life of the flower, its vigor and profusion of strong-stemmed flowers, its abundant foliage, its above average hardiness and disease resistance for a yellow rose; its true grandiflora habit; its classically spiraled flower; its abundant production of basal canes and its nearly continual production of flowers throughout the growing season.

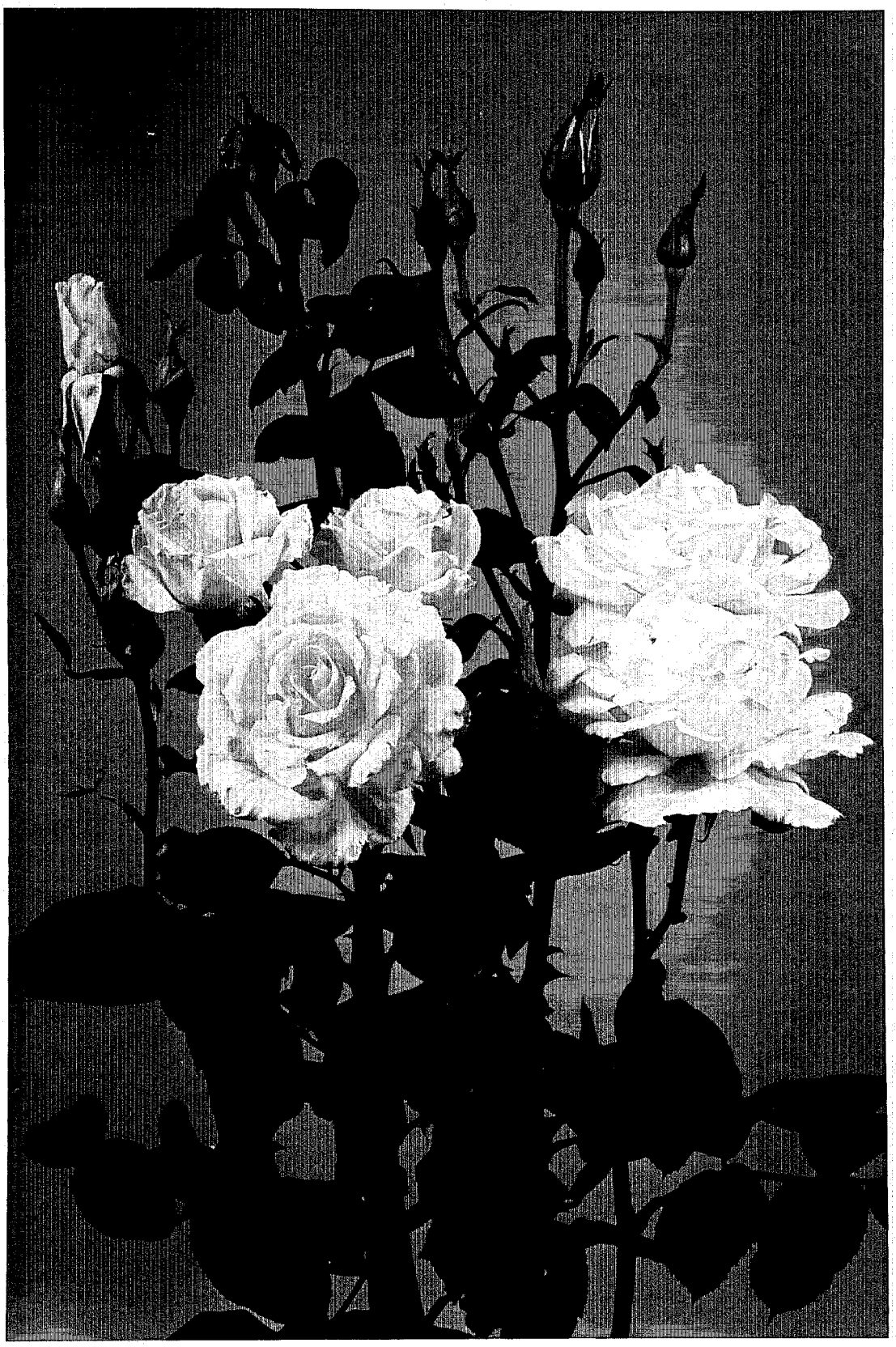

* * * * *